United States Patent
Li et al.

(10) Patent No.: US 11,380,960 B2
(45) Date of Patent: Jul. 5, 2022

(54) SURFACE MOUNT ANGLED BATTERY

(71) Applicant: LENOVO (Singapore) PTE. LTD., New Tech Park (SG)

(72) Inventors: Scott Wentao Li, Cary, NC (US); Robert James Kapinos, Durham, NC (US); Robert James Norton, Jr., Raleigh, NC (US); Russell Speight VanBlon, Raleigh, NC (US)

(73) Assignee: Lenovo (Singapore) PTE. LTD., New Tech Park (SG)

( * ) Notice: Subject to any disclaimer, the term of this patent is extended or adjusted under 35 U.S.C. 154(b) by 287 days.

(21) Appl. No.: 16/587,597

(22) Filed: Sep. 30, 2019

(65) Prior Publication Data

US 2021/0098754 A1 Apr. 1, 2021

(51) Int. Cl.
| | |
|---|---|
| *H01M 50/213* | (2021.01) |
| *H01M 10/052* | (2010.01) |
| *H01M 50/10* | (2021.01) |
| *H01M 50/24* | (2021.01) |

(52) U.S. Cl.
CPC ....... *H01M 50/213* (2021.01); *H01M 10/052* (2013.01); *H01M 50/10* (2021.01); *H01M 50/24* (2021.01); *H01M 2220/30* (2013.01)

(58) Field of Classification Search
CPC .. H01M 50/213; H01M 50/10; H01M 10/052; H01M 2220/30; Y02E 60/10; A61B 5/681; A61B 2560/0214; A61B 5/00
See application file for complete search history.

(56) References Cited

U.S. PATENT DOCUMENTS

| | | | |
|---|---|---|---|
| 2016/0056498 A1* | 2/2016 | Flitsch | H01M 10/058 29/623.4 |
| 2016/0278203 A1* | 9/2016 | Nakayama | A44C 5/0053 |
| 2017/0005504 A1* | 1/2017 | Rho | G04G 17/04 |

OTHER PUBLICATIONS

"Novel LiPo Battery—for your special shape", LiPol Batter Co. ltd. https://www.lipolbattery.com/Novel-LiPo-Battery. html, downloaded on Jan. 30, 2019, know about as early as Jul. 30, 2019., pp. 1-3.

* cited by examiner

*Primary Examiner* — Maria Laios
*Assistant Examiner* — Grace Ann Kenlaw
(74) *Attorney, Agent, or Firm* — Kunzler Bean & Adamson

(57) ABSTRACT

For a surface mount angled battery, the angled battery includes a proximal end with a proximal axis and a distal end with a distal axis. The distal axis is angled at a conforming angle at least 45 degrees from the proximal axis. A connector secures the angled battery to a receiver on a wearable monitoring device. Power contacts contact to power receptors on the wearable monitoring device.

20 Claims, 7 Drawing Sheets

SURFACE MOUNT ANGLED BATTERY

FIELD

The subject matter disclosed herein relates to power modules and more particularly relates to surface mounted angled battery.

BACKGROUND

Wearable devices must be powered and recharged.

BRIEF SUMMARY

An apparatus for supplying power to a wearable monitoring device is disclosed. The apparatus includes an angled battery, a connector, and power contacts. The angled battery includes a proximal end with a proximal axis and a distal end with a distal axis, wherein the distal axis is angled at a conforming angle at least 45 degrees from the proximal axis. The connector secures the angled battery to a receiver on a wearable monitoring device. The power contacts contact to power receptors on the wearable monitoring device. A system and method also perform the functions of the apparatus.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise. The term "and/or" indicates embodiments of one or more of the listed elements, with "A and/or B" indicating embodiments of element A alone, element B alone, or elements A and B taken together.

The schematic flowchart diagrams and/or schematic block diagrams in the Figures illustrate the architecture, functionality, and operation of possible implementations of apparatuses, systems, and methods according to various embodiments. It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

Figure 1A:
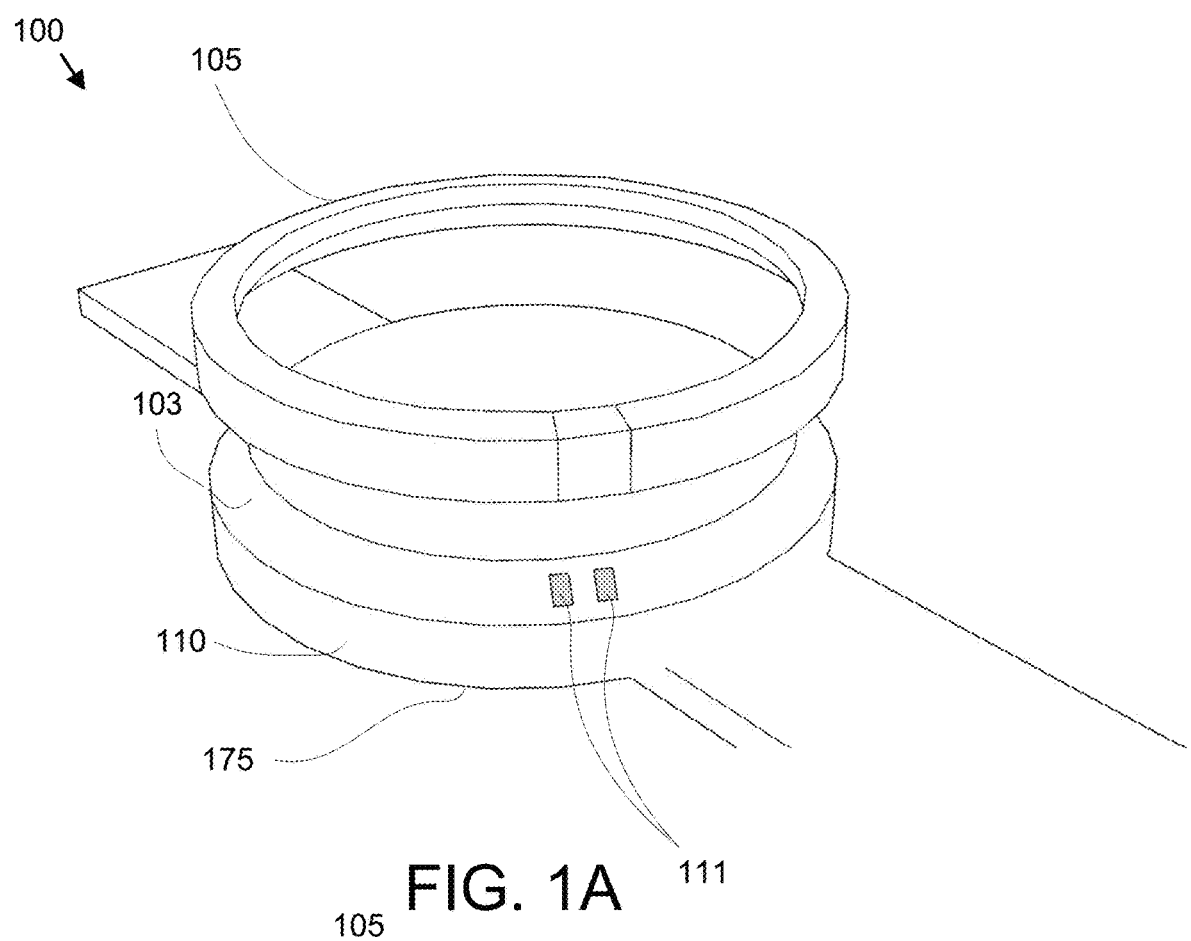
FIG. 1A is a perspective drawing illustrating one embodiment of a wearable system.

FIG. 1A is a perspective drawing illustrating one embodiment of a wearable system 100. In the depicted embodiment, a wearable monitoring device 110 is shown. The wearable monitoring device 110 may be worn on a user's wrist or other part of the user's body. A bottom 175 of the wearable monitoring device 110 may be positioned against the user. The wearable monitoring device 110 may continuously monitor the user. As a result, the wearable monitoring device 110 is battery-powered.

Unfortunately, when the battery of the wearable monitoring device 110 must be recharged, the user must either remove the wearable monitoring device 110 or remain close to a charging station, charging cable, and/or charging zone. None of these options may be desirable.

The embodiments provide an angled battery 105 for powering and/or recharging the wearable monitoring device 110. The angled battery 105 conforms to an outer surface 103 of the wearable monitoring device 110. As a result, the angled battery 105 may be affixed to the wearable device 110 to provide power to and/or recharge the wearable monitoring device 110 through power receptors 111 as will be described hereafter.

Figure 1B:
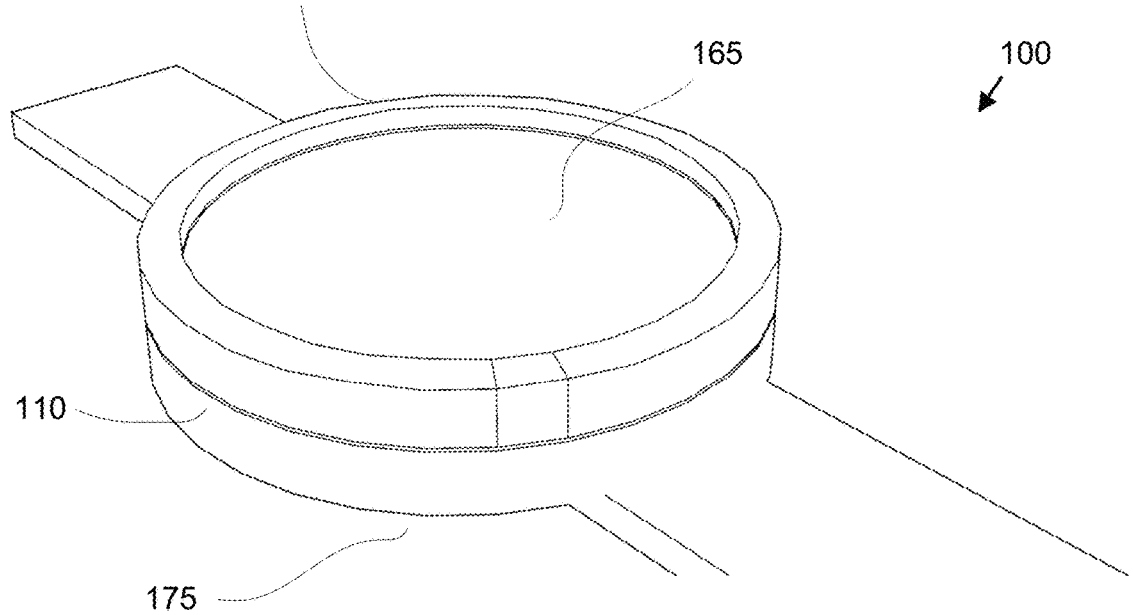
FIG. 1B is a perspective drawing illustrating one alternate embodiment of a wearable system.

FIG. 1B is a perspective drawing illustrating one alternate embodiment of the wearable system 100. The wearable monitoring device 110 of FIG. 1A is shown with the angled battery 105 affixed to the wearable monitoring device 110. Because the angled battery 105 is not a fixed to the bottom 175 of the wearable monitoring device 110, contact between the wearable monitoring device 110 and the user is not interrupted.

The angled battery 105 is further angled around the display 165 of the wearable monitoring device 110. As a result, the user may continue to access the display 165. Thus the wearable monitoring device 110 continues to monitor and gather data without interruption, and may present information to the user.

Figure 1C:
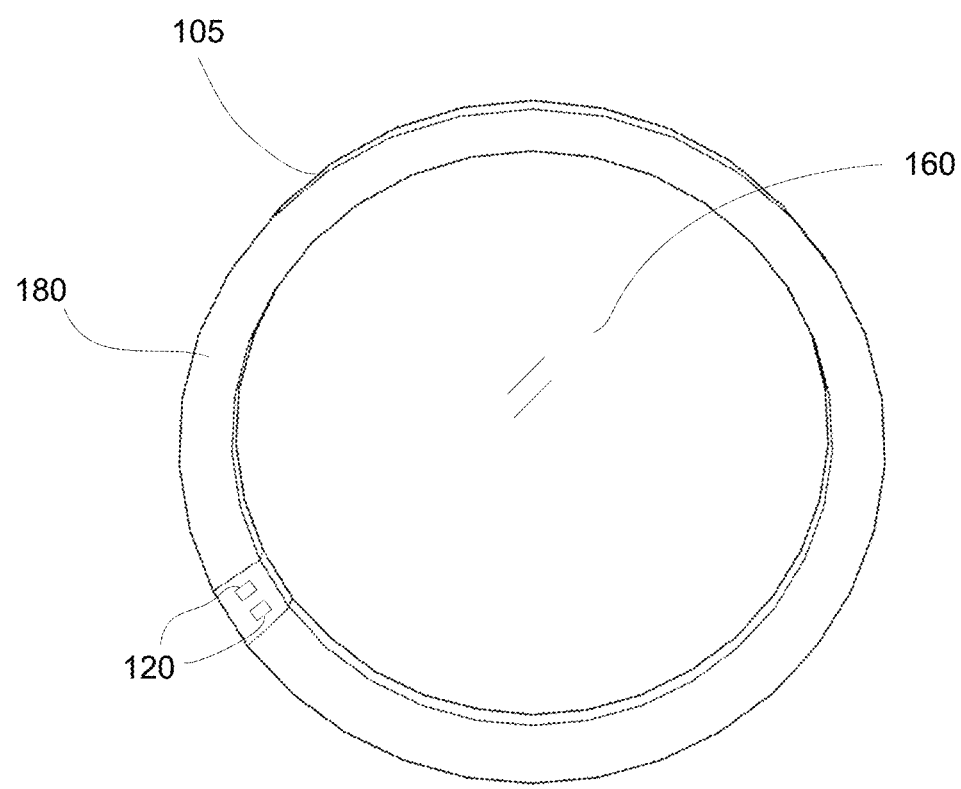
FIG. 1C is a perspective drawing illustrating one embodiment of an angled battery.

FIG. 1C is a perspective drawing illustrating one embodiment of the angled battery 105. The angled battery 105 of FIGS. 1A-B is shown from the bottom. A bottom 180 of the angled battery 105 conforms to the outer surface 103 of the wearable monitoring device 110. In one embodiment, the angled battery 105 conforms to the outer surface 103 of the wearable monitoring device 110 if adjacent portions of the outer surface 103 and the bottom 180 are within a specified range of each other. The specified range may be 0.1 to 3.5 millimeters (mm). In the depicted embodiment, the angled battery 105 includes power contacts 120 that connect to the power receptors 111 on the wearable monitoring device 110. Each power contact 120 may be connected to a pole of the angled battery 105.

In one embodiment, the power contacts 120 are integrated in connectors. In addition, the power receptor 111 may be integrated in a receiver. The connector power contacts 120 may engage with the receiver power receptors 111 to secure the angled battery 105 to the wearable monitoring device 110.

In one embodiment, the angled battery 105 includes a transparent shield 160. The transparent shield 160 may protect the wearable monitoring device 110. In addition, the transparent shield 160 may allow the user to view the display 165.

Figure 2:
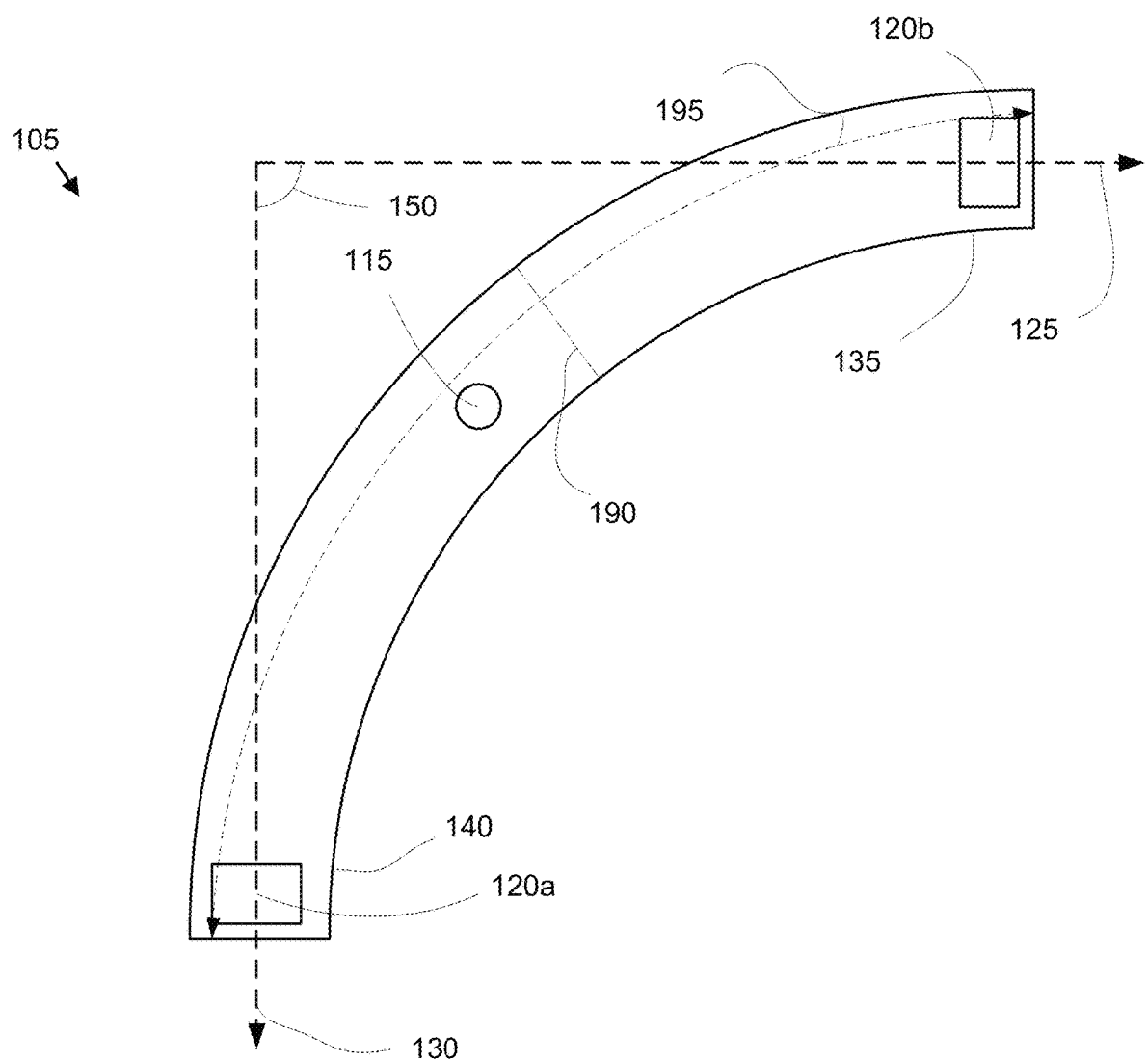
FIG. 2 is a schematic top view diagram illustrating one embodiment of an angled battery.

FIG. 2 is a schematic top view diagram illustrating one embodiment of the angled battery 105. The angled battery 105 comprises a proximal end 135 and a distal end 140. The proximal end 135 includes a proximal axis 125. The distal end 140 includes a distal axis 130. The proximal axis 125 may be coplanar with the distal axis 130. Alternatively, the proximal axis 125 is not coplanar with the distal axis 130. The distal axis 130 is angled at a conforming angle 150 from the proximal axis 125. The conforming angle 150 may be at least 45 degrees. In the depicted embodiment, the conforming angle 150 is 90 degrees. Table 1 lists alternate conforming angles 150.

TABLE 1

| Conforming Angles 150 |
| --- |
| 50 degrees |
| 60 degrees |
| 70 degrees |
| 80 degrees |
| 120 degrees |
| 135 degrees |
| 180 degrees |
| 270 degrees |
| 360 degrees |

In the depicted embodiment, one power contact 120*a* is embedded in the distal end 140 and another power contact 120*b* is embedded in the proximal end 135. The angled battery 105 includes a connector 115 that secures the angled battery 105 to a receiver (not shown) on the wearable monitoring device 110. Although one connector 115 is shown, any number of connectors 115 may be employed. The connector 115 and receiver are described in more detail in FIGS. 4A-D.

The angled battery 105 has an angled length 195. The angled length 195 comprises the overall length of the angled battery 105 from proximal end 135 to distal end 140. The angled length may be at least four times greater than an battery width 190. Table 2 lists alternate ratios of the angled length 105 to battery width 190.

TABLE 2

| Angled Length 195 | Battery Width 190 |
| --- | --- |
| 5 | 1 |
| 6 | 1 |
| 7 | 1 |
| 8 | 1 |
| 9 | 1 |
| 10 | 1 |
| 10 | 1.5 |
| 8 | 1.5 |

In one embodiment, the angled battery 105 is a rechargeable lipo polymer battery. In addition, the angled battery 105 may comprise a plurality of lithium ion batteries connected in series. The angled battery 105 may be packed in a case. For example, the angled battery may be disposed in a molded case.

In one embodiment, the angled battery 105 is sealed with a coating. For example, the angled battery 105 may be sealed in a polyurethane coating.

Figure 3A:
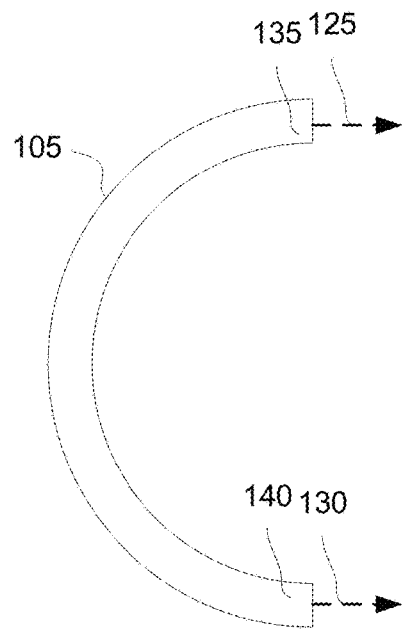
FIGS. 3A-D are schematic top view diagrams illustrating embodiments of angled batteries.
Figure 3B:
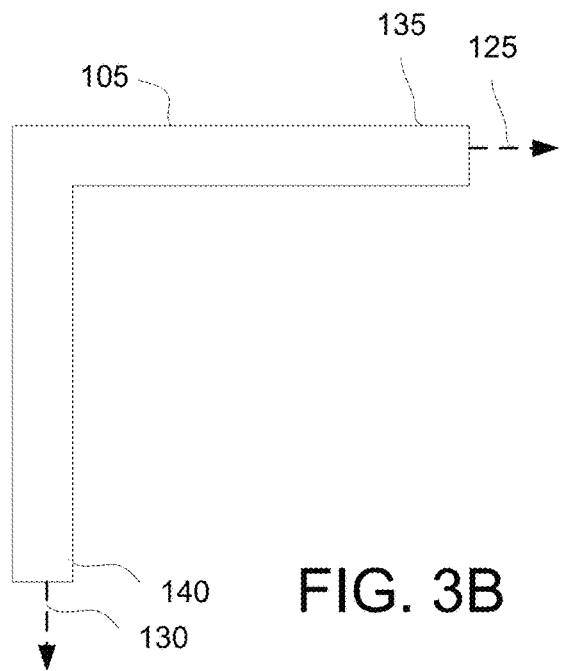
Figure 3C:
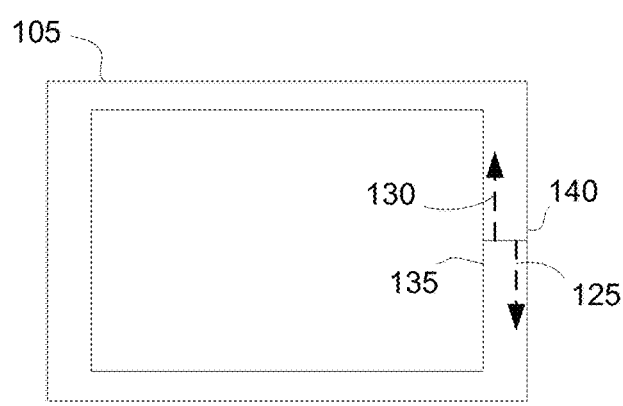
Figure 3D:
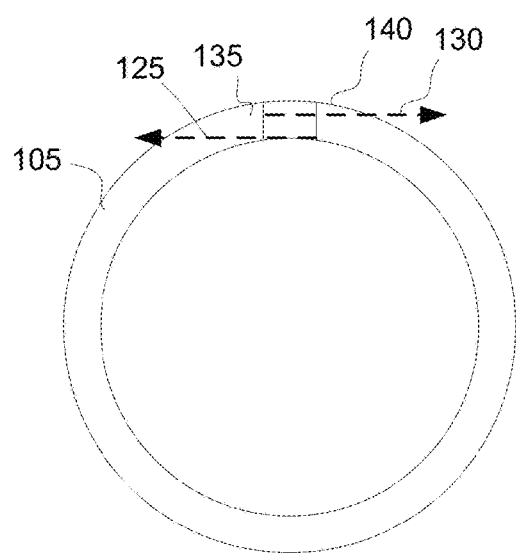

FIGS. 3A-D are schematic top view diagrams illustrating embodiments of angled batteries 105. In FIG. 3A, the angled battery 105 forms a semi-circle. In FIG. 3B, the angled battery 105 forms a right angle. In FIG. 3C, the angled battery 105 forms a rectangle. In FIG. 3D, the angled battery 105 forms a circle. The proximal ends 135, distal ends 140, and corresponding distal axes 130 and proximal axes 125 are shown. As shown in FIGS. 3C-D, the distal axes 130 and proximal axes 125 may be a oriented in opposite directions with conforming angles 150 of at least 180 degrees. Proximal ends 135 and distal ends 140 may abut as shown in FIG. 3C.

FIGS. 4A-D are schematic top view diagrams illustrating embodiments of connectors 115 and receivers 107. One or more connectors 115 are disposed on each angled battery 105. A corresponding receiver 107 is disposed on the wearable monitoring device 110. The connector 115 may be selected from the group consisting of a magnet, a prong, a hole, and a clip. The receiver 107 may be selected from the group consisting of a magnet, a hole, a prong, and a bracket.

Figure 4A:
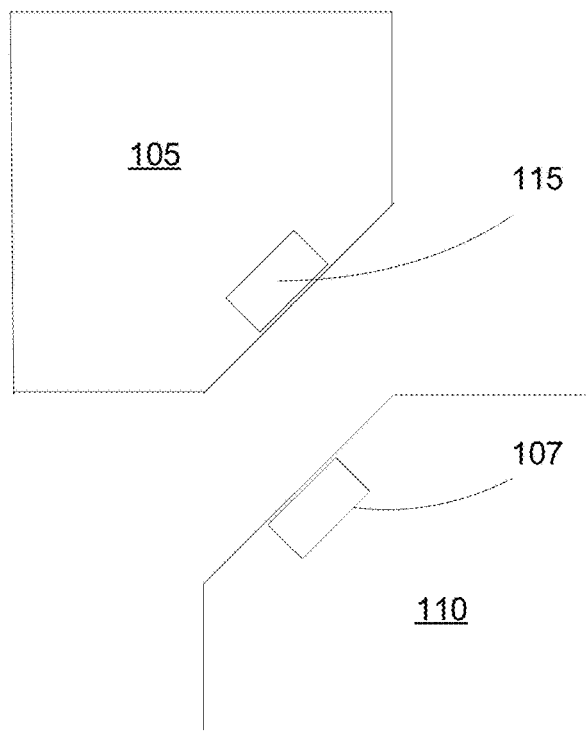
FIGS. 4A-D are schematic top view diagrams illustrating embodiments of connectors and receivers.

FIG. 4A illustrates a magnet connector 115 and a magnet receiver 107. The magnets of the connector 115 and receiver 107 may secure the angled battery 105 to the wearable monitoring device 110.

Figure 4B:
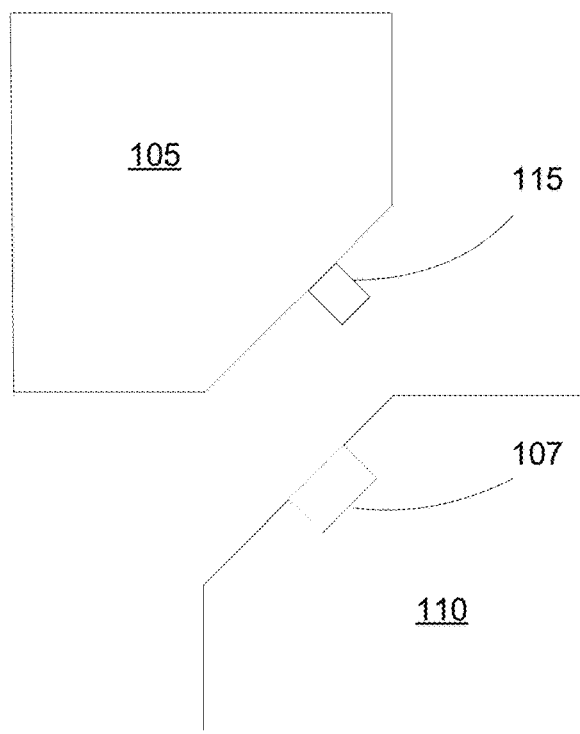

FIG. 4B illustrates a prong connector 115 and a hole receiver 107. The prong connector 115 may clip into the hole receiver 107 to secure the angled battery 105 to the wearable monitoring device 110.

Figure 4C:
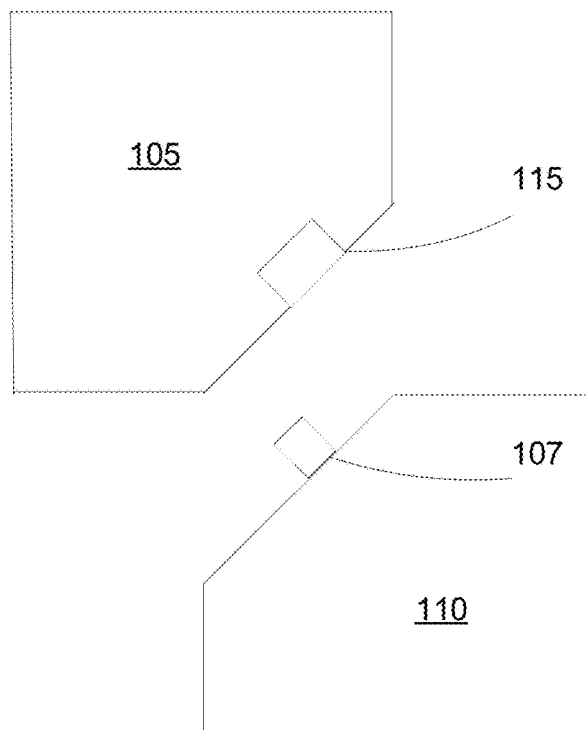

FIG. 4C illustrates a hole connector 115 and a prong receiver 107. The prong receiver 107 may clip into the hole connector 115 to secure the angled battery 105 to the wearable monitoring device 110.

Figure 4D:
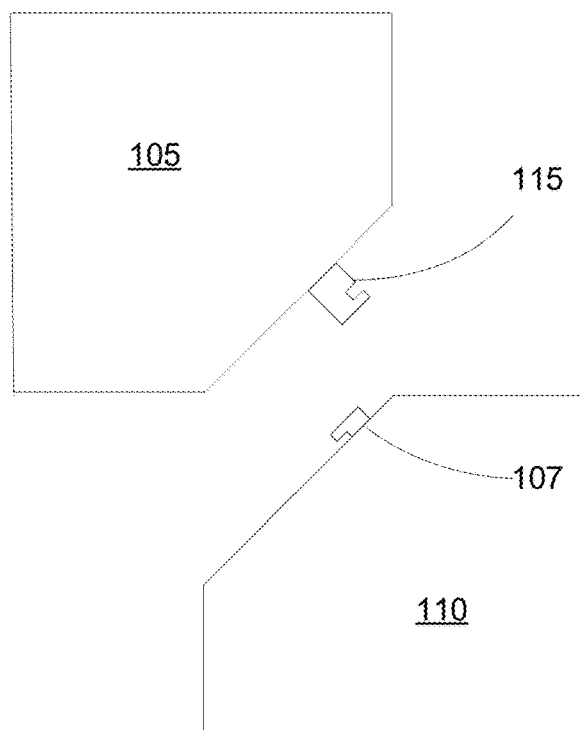

FIG. 4D illustrates a clip connector 115 and a bracket receiver 107. The clip connector 115 may engage the bracket receiver 107 to secure the angled battery 105 to the wearable monitoring device 110.

Figure 5:
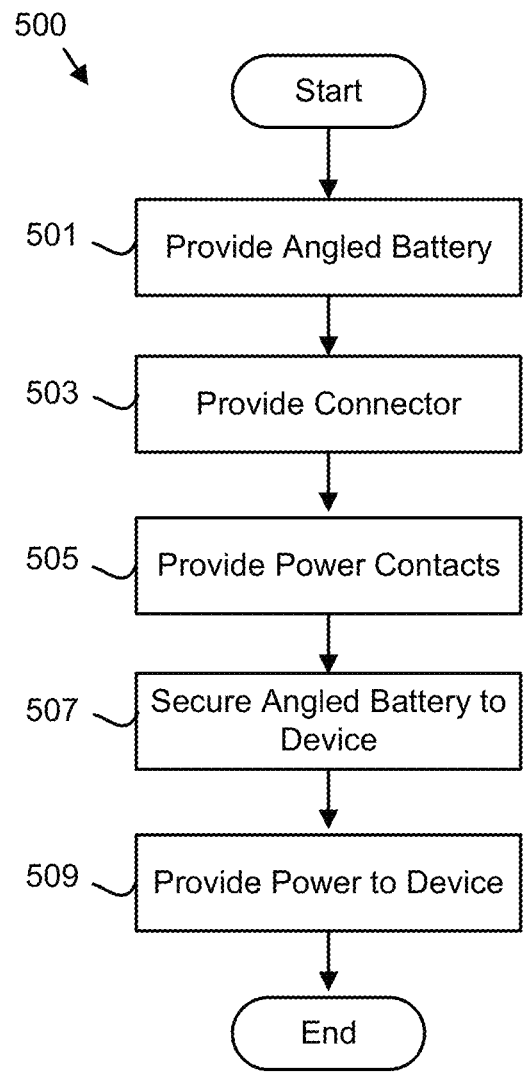
FIG. 5 is a schematic flow chart diagram illustrating one embodiment of a power provision method.

FIG. 5 is a schematic flow chart diagram illustrating one embodiment of a power provision method 500. The method 500 may be performed by the angled battery 105.

The method 500 provides 501 the angled battery 105. In addition, the method 500 provides 503 the connector 115. The method 500 further provides 505 the power connectors 120. The connector 115 may secure 507 the angled battery 105 to the wearable monitoring device 110 by engaging with the receiver 107. Secured 507 to the wearable monitoring device 110, the angled battery 105 may provide 509 power to the wearable monitoring device 110 via the power connectors 120, charging and/or powering the wearable monitoring device 110.

As a result, the wearable monitoring device 110 may be charged without interrupting the monitoring of the user by the wearable monitoring device 110. In addition, the wearable monitoring device 110 may be powered while the wearable monitoring device 110 remains usable by the user and the user is not constrained by a power station, charger, or charging zone. Thus, the utility of the wearable monitoring device 110 is improved.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
    an angled battery comprising a proximal end with a proximal axis and a distal end with a distal axis, the angled battery forming a loop and conforming to an outer surface of a wearable monitoring device wherein a display of the wearable device is accessible through a center of the angled battery and the angled battery is removable from the wearable device without interrupting contact between the wearable device and a wearer;
    a connector that secures the angled battery to a receiver on the wearable monitoring device; and
    power contacts that contact to power receptors on the wearable monitoring device.
2. The apparatus of claim 1, wherein the angled battery loop forms a circle.
3. The apparatus of claim 1, wherein the angled battery loop forms a rectangle.
4. The apparatus of claim 1, wherein the connector is selected from the group consisting of a magnet, a prong, a hole, and a clip.
5. The apparatus of claim 1, wherein the power contacts are integrated in the connector.
6. The apparatus of claim 1, wherein the angled battery is a rechargeable lithium polymer battery.
7. The apparatus of claim 1, wherein the angled battery is packed in a case.
8. The apparatus of claim 1, wherein the angled battery is sealed with a coating.
9. The apparatus of claim 1, wherein the angled battery charges and/or powers the wearable monitoring device.
10. The apparatus of claim 1, wherein the angled battery further comprises a transparent shield.
11. A system comprising:
    a wearable monitoring device comprising a display a receiver, and power receptors;
    an angled battery comprising a proximal end with a proximal axis and a distal end with a distal axis, the angled battery forming a loop and conforming to an outer surface of the wearable monitoring device wherein the display of the wearable device is accessible through a center of the angled battery and the angled battery is removable from the wearable device without interrupting contact between the wearable device and a wearer;
    a connector that secures the angled battery to the receiver on the wearable monitoring device; and
    power contacts that contact to the power receptors on the wearable monitoring device.
12. The system of claim 11, wherein the angled battery loop forms a circle.
13. The system of claim 11, wherein the angled battery loop forms a rectangle.
14. The system of claim 11, wherein the connector is selected from the group consisting of a magnet, a prong, a hole, and a clip and the receiver is selected from the group consisting of a magnet, a hole, a prong, and a bracket.
15. The system of claim 11, wherein the power contacts are integrated in the connector.
16. The system of claim 11, wherein the angled battery is a rechargeable lithium polymer battery.
17. The system of claim 11, wherein the angled battery further comprises a transparent shield.
18. A method comprising:
    providing an angled battery comprising a proximal end with a proximal axis and a distal end with a distal axis, the angled battery forming a loop and conforming to an outer surface of a wearable monitoring device wherein a display of the wearable device is accessible through a center of the angled battery and the angled battery is removable from the wearable device without interrupting contact between the wearable device and a wearer;
    providing a connector that secures the angled battery to a receiver on the wearable monitoring device; and
    providing power contacts that contact to power receptors on the wearable monitoring device, wherein the angled battery charges and/or powers the wearable monitoring device with the power contacts through the power receptors.
19. The method of claim 18, wherein the angled battery is a rechargeable lithium polymer battery.
20. The method of claim 18, wherein the angled battery further comprises a transparent shield.

* * * * *